United States Patent [19]

Thornfeldt

[11] Patent Number: 5,231,087

[45] Date of Patent: Jul. 27, 1993

[54] TREATMENT OF SKIN DISEASES AND TUMORS WITH ESTERS AND AMIDES OF MONOCARBOXYLIC ACIDS

[75] Inventor: Carl R. Thornfeldt, Ontario, Oreg.

[73] Assignee: Cellegy Pharmaceuticals, Inc., Novato, Calif.

[21] Appl. No.: 823,946

[22] Filed: Jan. 22, 1992

Related U.S. Application Data

[63] Continuation-in-part of Ser. No. 519,033, May 4, 1990, abandoned, which is a continuation-in-part of Ser. No. 369,175, Jun. 21, 1989, abandoned, which is a continuation-in-part of Ser. No. 221,690, Jul. 20, 1988, abandoned, which is a continuation-in-part of Ser. No. 168,727, Mar. 16, 1988, abandoned.

[51] Int. Cl.⁵ ............................................. A61K 31/715
[52] U.S. Cl. ..................................... 514/53; 514/546; 514/547; 514/552; 514/625; 514/627; 514/629; 514/859; 514/863
[58] Field of Search ................. 514/53, 546, 547, 552, 514/625, 627, 629

[56] References Cited

U.S. PATENT DOCUMENTS

| | | | |
|---|---|---|---|
| 3,535,422 | 10/1970 | Cox et al. | 424/164 |
| 4,557,935 | 12/1985 | Ekenstam et al. | 424/130 |
| 5,057,500 | 10/1991 | Thornfeldt | 514/53 |
| 5,057,501 | 10/1991 | Thornfeldt | 514/53 |

FOREIGN PATENT DOCUMENTS

| | | |
|---|---|---|
| 77395/87 | 3/1983 | Australia |
| 67478/87 | 7/1987 | Australia |
| B-49876/90 | 8/1990 | Australia |

OTHER PUBLICATIONS

Calabresis, P., et al., *Goodman and Gilman, The Pharmacological Basis of Therapeutics*, Eighth Edition, pp. 1205-1207, Pregamon Press, New York (1990).

Kato, A., et al., "Antitumor Activity of Monoglycerides and Other Esters of Fatty Acids", *J. of Antibiotics*, vol. XXII, No. 2, pp. 83-84 (Feb. 1969).

Kabara, J., et al., "Examinations on Antitumor, Immunological, and Plant-Growth Inhibitory Effects of Monoglycerides of Caprylic, Capric, and Lauric Acids and Related Compounds", *The Pharmacological Effect of Lipids II*, The American Oil Chemists' Society, Champaign, Ill. (ed. Kabara), Chapter 23, pp. 263-267 (1985).

Stryer, L., *Biochemistry*, Third Ed. p. 988, Freeman and Co., New York (1988).

*Primary Examiner*—Leonard Schenkman

[57] ABSTRACT

Noninfectious inflammatory and hyperpigmentation skin diseases, thermal injuries and premalignant skin tumors induced by radiation or virus, in both humans and animals, are treated with topical formulations of an ester or amide of a monocarboxylic acid, the acid moiety of which is 9 to 18 carbon atoms.

16 Claims, No Drawings

TREATMENT OF SKIN DISEASES AND TUMORS WITH ESTERS AND AMIDES OF MONOCARBOXYLIC ACIDS

CROSS-REFERENCE TO RELATED APPLICATIONS

This application is a continuation-in-part of application Ser. No. 07/519,033, filed May 4, 1990, now abandoned which is a continuation-in-part of application Ser. No. 07/369,175, filed Jun. 21, 1989, now abandoned, which is a continuation-in part of application Ser. No. 07/221,690, filed Jul. 20, 1988, now abandoned, which is a continuation-in-part of application Ser. No. 07/168,727, filed Mar. 16, 1988, now abandoned.

BACKGROUND OF THE INVENTION

Certain classes of noninfections inflammatory and hyperpigmentation diseases of the skin, thermal injuries of the skin, and premalignant skin tumors induced by ultraviolet or x-ray radiation or viruses, particularly those diseases which are multifactorial with a genetic predisposition, have yet to find a therapy which is fully satisfying. The standard therapies generally consist of the administration of antimicrobial agents which, depending on the disease, result in varying degrees of clearing of the disease condition. None of them however completely clear the disease.

Prominent among these diseases are the ichthyoses, rosacea, acne vulgaris, psoriasis, various types of dermatitis, melasma and actinic lentigos, actinic keratoses, Bowenoid papulosus, condylomatous dysplasia, cervical carcinoma, Bowen's disease and lentigo maligna.

The ichthyoses are a group of uncommon genetic diseases characterized by extreme scaling due to abnormal stratum corneum and epidermal function. Patients suffering from ichthyoses require lifelong daily therapy. Severe disfigurement occurs in the less common inflammatory types such as congenital ichthyosiform erythroderma, lamellar and X-linked ichthyosis, and epidermolytic hyperkeratosis. Microbial infection occurs in only two of the inflammatory types, and infrequently. Current treatments for the ichthyoses include retinoids and α-hydroxy acids. Each of these is effective in only a minority of patients, and even in those cases where they are effective, these treatments are often toxic, either topically, systemically, or both.

Rosacea is an inflammatory disease due to abnormal sensitivity of the vasculature. Rosacea often results in secondary sebaceous gland hyperplasia and inflammation producing characteristic skin lesions. Treatments for rosacea generally involve the administration of anti-inflammatory antibiotics such as Metronidizole.

Acne vulgaris is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and Pitrosporum ovale, a yeast. Thus released, the lipases cause damage to the gland structure and surrounding tissue, and this results in the formation of inflammatory papules, pustules, and cysts. The appearance of comedos, which are free of these microbes and inflammation, is a further characteristic of this disease. In some patients suffering from the disease, the only manifestation is noninflammatory lesions. Among those with inflammatory lesions, however, comedos appear in all cases. The most common treatments for acne vulgaris are oral and topical antibiotics and retinoids, topical forms of sulicylic acid, sulfur, and benzoyl peroxide, and oral antiandrogens.

Psoriasis in an inflammatory multifactorial disease characterized by epidermal hyperproliferation, disruption of the stratum corneum, and local immunologic anomalies, with microbial infection occurring in half the lesions. About half of psoriasis lesions have positive cultures for *Staphylococcus aureus*. β-Hemolytic Streptococcus is known to cause guttate psoriasis. Psoriasis lesions are sharply demarcated, firm erythematous plaques usually with white scale. These plaques occur predominately on knees, elbows, scalp, genitalia, and buttocks. Current treatments consist of topical applications of corticosteroids, tar, anthralin, methotrexate, azathioprine, etretinate, psoralens plus ultraviolet A light, and tar plus ultraviolet B light. Antimicrobial agents along rarely produce a beneficial effect.

Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. Lesions of atopic and contact dermatitis usually occur on the face, neck, and flexural surfaces. In most patients, there is also a heavy growth of *Staphylococcus aureus* and β-hemolytic Streptococcus. Diaper dermatitis results from contact irritation to urine and feces followed by opportunistic infections by mixed bacterial and yeast organisms. Contact dermatitis results from irritation or allergy to chemicals or toxins applied to the skin intentionally or by accident. Current therapies for these various forms of dermatitis include topical and systemic corticosteroids, antipruritics, antibiotics and topical tar. Antibiotics when used along have no more than a mild therapeutic value, however.

Seborrheic dermatitis is characterized by poorly demarcated, scaley erythematous patches with yellowish greasy scales. "Dandruff" is a mild form of this condition, localized to the scalp. This disease may involve any one, several, or all of the following sites: scalp, eyebrows, glabella, paranasal and chin folds, ears and retroauricular sulci, presternal interscapular regions, pubic regions, and intergluteal folds. Pityrosporum ovale, a yeast, has been shown to play a significant role in 75% of patients afflicted with sebhorreic dermatitis. Present therapies for this disease include corticosteroids, tar, sulfur, and antibiotics, including antiyeast agents. One antiyeast agent, ketoconazole, has been reported to improve or clear seborrheic dermatitis lesions in about 75% of the patients in a group study. Other antimicrobial agents have only a mild therapeutic effect upon the lesions.

Melasma and actinic lentigos result from melanocytic hyperplasia. Melasma occurs only on the face while the lentigos may occur at any site, especially areas exposed to sun. The only effective approved treatment is hydroquinone. In some cases, however, this product results in dyspigmentation.

Actinic keratoses are superficial inflammatory premalignant tumors arising on sun-exposed and irradiated skin. The lesions are erythematous to brown with variable scaling. Current therapies include excisional and cryosurgery, 5-fluorouracil cream and chemical peels. These treatments are painful, however, and often produce cosmetically unacceptable dyspigmentation.

Bowenoid papulosus is a tumor of the genitalia induced by premalignant wart viruses and usually afflicting men. Condylomatous dysplasia and cervical carcinoma in situ are premalignant tumors of the female genitalia, also induced by wart viruses. Known treatments for all three of these tumors are cryosurgery, 5-fluorouracil, trichloroacetic acid, podophyllin and interferon. These treatments are painful, however, and not very effective, and often fail to produce long-term remission. Furthermore, when used against Bowenoid papulosus, these treatments have been shown in some cases to produce cosmetically unacceptable dyspigmentation.

Bowen's disease is a superficial intraepidermal tumor of keratinocytes most commonly caused by ultraviolet irradiation. Approximately 5% of Bowen's disease tumors metastasize as squamous cell carcinoma. These tumors frequently cover large areas of the skin. Current treatments consist of excisional and cryosurgery and 5-fluorouracil cream.

Lentigo maligna is a premalignant tumor of melanocytes usually occurring on sun-exposed, usually facial skin of elderly patients. In up to 30% of cases of this disease, the tumors progress to invasive melanoma cancer. These tumors frequently cover large surface areas. Treatment of lentigo maligna usually consists of excisional or cryosurgery, although the application of azelaic acid is also effective in some patients.

Certain prior issued patents may be of potential relevance to this invention. U.S. Pat. No. 4,292,326 (Nazarro-Porro, Sep. 29, 1981), U.S. Pat. No. 4,386,104 (Nazarro-Porro, May 31, 1983), and U.S. Pat. No. 4,713,394 (Thornfeldt, Dec. 15, 1987), disclose the use of certain dicarboxylic acids as therapeutic agents for a variety of skin diseases. U.S. Pat. No. 4,067,997 (Kabara, Jan. 10, 1978) discloses the activity against yeast, fungus, and bacteria of a synergistic combination of a 12-carbon monocarboxylic acid glycerol ester and a phenolic compound, used as a food preservative. U.S. Pat. No. 4,557,935 (af Ekenstam, et al., Dec. 10, 1985) discloses the germicidal activity of hydrogen peroxide in a formulation with the monoglyceride esters of lauric and myristic acids. U.S. Pat. No. 3,535,422 (Cox, et al., Oct. 20, 1970) discloses the synergistic activity of benzoyl peroxide, sulfur and organic emollients to treat acne, stating that the organic emollients, of which glycerol esters of monocarboxylic acids are included as examples, are stabilizers of the active ingredients rather than active ingredients themselves.

SUMMARY OF THE INVENTION

It has now been discovered that esters and amides of certain aliphatic monocarboxylic acids have an inherent therapeutic activity against the skin conditions listed above, and can be used as the sole or primary active therapeutic agent in effective treatments for these conditions, particularly as topical formulations. These treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats. Among such animals, dogs are of particular interest.

DETAILED DESCRIPTION OF THE INVENTION AND PREFERRED EMBODIMENTS

The monocarboxylic acid portions of the compounds used in the practice of the present invention are those of 9 to 18 carbon atoms, inclusive. Such acids include straight-chain and branched-chain species, as well as saturated and unsaturated species, including species with multiple unsaturation sites. Preferred compounds are those in which the acid portions are straight-chain aliphatic acids, either saturated or unsaturated. Also preferred are species containing 10 to 15 carbon atoms in the acid portion. Examples of straight-chain acids are pelargonic (n-nonanoic), capric (n-decanoic), n-undecanoic, lauric (n-dodecanoic), n-tridecanoic, myristic (n-tetradecanoic), myristoleic (cis-tetradec-9-enoic), palmitic (n-hexadecanoic), palmitoleic (cis-hexadec-9-enoic), n-hexadecanoic, oleic (cis-octadec-9-enoic), linoleic (9,12-octadecadienoic), linolenic (9,12,15-octadecatrienic), and n-octadecanoic acids. Lauric acid is particularly preferred.

For those embodiments of the invention in which the active agent is an ester of such acids, such embodiments include glycerides and polyglycerides such as monoglycerides, triglycerides, hexaglycerides, and decaglycerides; as well as esters formed from methanol, ethanol, propylene glycol, polyethylene glycol, ethanol, and sorbitol; and saccharides such as sucrose. Specific examples are 1-monolaurin, 2-monolaurin, monocaprin, monomyristin, monolinolein; diglycerol laurate; triglycerol caprylate, pelargonate, caprate, and laurate; hexaglycerol caproate, caprylate, pelargonate, caprate and laurate; decaglycerol butyrate, caprylate, pelargonate, caprate, and laurate; sucrose caprylate, caprate, laurate, myristate, palmitate, elaidate, oleate, and linoleate. The term "monolaurin" will be used herein as an abbreviation for 1-monolaurin.

For those embodiments in which the active agent is an amide, prominent examples are capratoylamide, laurylamide, myristoleylamide, and palmitoleylamide, capratoyl-N,N-dimethylamide, lauryl-N,N-dimethylamide, myristoleyl-N,N-dimethylamide, palmitoleyl-N,N-dimethylamide, linoleyl-N,N-dimethylamide, octadecanoyl-N,N-dimethylamide. A preferred example is lauryl-N,N-dimethylamide.

The ester or amide of the monocarboxylic acid as defined above is effective on its own and may thus be used as the sole active component in a dermatological formulation. Such a formulation may be applied topically to disease sites, and may include any of the various known mixtures and combinations of inert compounds which are commonly used in topical dermatological formulations to permit even spreading of the active ingredient over the affected area. Examples of formulations are creams, lotions, solutions, ointments, unguents and pastes.

The concentration of the ester or amide in the formulation may vary over a wide range. The concentration may indeed range as high as the upper limit of dissolvability in any given formulation. In most cases, best results are achieved within a concentration within the range of about 1% to about 35% by weight, preferably from about 3% to about 15% by weight.

Compounds which enhance the penetration of the stratum corneum are usually included in dermatologic formulations but do not affect the disease itself. Examples of such compounds are propylene glycol, sodium lauryl sulfate, dimethylamide, N-methyl-2-pyrrolidone, and Azone (Nelson Research, Irvine, California).

The term "therapeutically effective amount" is used herein when describing the amount of dermatological formulation to be applied in any particular case, and when so used denotes any amount which will cause a substantial improvement in a disease condition (such as for example a subsidence of a lesion) when applied to the affected area repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The following examples are offered for purposes of illustration, and are intended neither to define nor limit the invention in any manner.

Examples 1 through 6 illustrate the preparation of topical formulations in accordance with the present invention.

EXAMPLE 1

A therapeutic ointment was prepared by dissolving 17.5 grams of 1-monolaurin (obtained from Lauricidin, Inc., Okemos, Mich.) in 10 mL of commercial isopropyl alcohol heated to 50° C. Commercial propylene glycol (7 mL) was the incorporated into the solution and the resulting mixture was cooled overnight at 24° C. The mixture was then worked into 100 g of Aquaphor (4-chloro-5-sulfamoyl-2',6'-salicyloxylidide, obtained from Beiersdorf, Inc., Norwalk Conn.) on a pill tile.

The resulting ointment is hereinafter referred to as Formula A.

EXAMPLE 2

A therapeutic ointment was prepared in a manner identical to that described in Example 1, except that 9 g of 1-monolaurin, 5 mL of isopropyl alcohol and 1 mL of propylene glycol were used.

The resulting ointment is hereinafter referred to as Formula B.

EXAMPLE 3

A therapeutic formulation was prepared by dissolving 17.5 g of 1-monolaurin in 52 mL of isopropyl alcohol mixed with 24 mL of propylene glycol and heated to 50° C.

The resulting formulation is hereinafter referred to as Formula C.

EXAMPLE 4

A therapeutic formulation was prepared in a manner identical to that described in Example 3, except that 24 g of 1-monolaurin, 52 mL of isopropyl alcohol and 24 mL of propylene glycol were used.

The resulting formulation is hereinafter referred to as Formula D.

EXAMPLE 6

A therapeutic formulation was prepared by mixing the following:

| | |
|---|---|
| 1-Monolaurin | 17.14% |
| SDA 40-2 (95%) | 10.00 |

-continued

| | |
|---|---|
| Poloxamer 407 | 7.00 |
| Oleyl Alcohol | 5.00 |
| Glycerin | 5.00 |
| White Wax | 3.50 |
| Methyl Paraben | 0.20 |
| Propyl Paraben | 0.10 |
| Ascorbyl Palmitate | 0.05 |
| Purified Water | 52.01 |

The resulting formulation is hereinafter referred to as Formula E.

EXAMPLE 6

A therapeutic formulation was made by dissolving 11 g of 1-monopalmitolein (Sigma Chemical) in 6 mL of isopropyl alcohol and heated to 50° C. Commercial propylene glycol (3 mL) was then incorporated into the solution, and the solution was cooled overnight at 24° C. The mixture was then worked into 100 g of Aquaphor on a pill tile.

The resulting ointment is hereinafter referred to as Formula F.

Examples 7 through 14 illustrate the therapeutic effects of these formulations.

EXAMPLE 7

Twenty-five human patients with grade I-III acne vulgaris were treated twice daily with Formula C for 12 weeks. Previously, the acne in all these patients had failed to completely clear upon the administration of standard topical and therapeutic agents. In several cases, isotretinoin had also been administered, and these treatments had failed as well. Treatment with Formula C, however, produced a 72% decrease in the number of inflammatory papules and pustules in the entire group of patients while only three of the patients experienced worsening of the disease.

EXAMPLE 8

Twenty-two human patients with refractory plaque type psoriasis vulgaris were treated for four weeks twice daily with Formula A. These patients had failed to respond to all other topical and oral psoriasis treatments. As a result of the administration of Formula A, 77% of the patients experienced 50% or better clearing of lesions, with complete clearing in six patients.

EXAMPLE 9

Ten human patients with refractory facial seborrheic dermatitis were treated twice daily with Formula B. These patients had previously failed to respond to topical corticosteroids, antifungals and antibiotics. As a result of the use of Formula B, all three gained complete resolution of the skin rash after three weeks of treatment.

EXAMPLE 10

Three human patients with refractory atopic dermatitis were treated with Formula A twice daily for six weeks. These patients had previously failed to respond to topical corticosteroids, tars, oral and topical antibiotics, and antihistamines. Treatment with Formula A produced complete clearing of the condition in all three patients.

EXAMPLE 11

Two human patients with refractory condyloma acuminata were treated with Formula D twice daily for six weeks. One completely cleared after two weeks of treatment; the other cleared after five weeks of treatment.

EXAMPLE 12

Five human patients with persistent melasma that had failed to be resolved by hydroquinone were treated for six weeks, twice daily, with Formula C. As a result, two of the five cases experienced complete resolution of the condition, two other improved by 75%, and the remaining one by 50%.

EXAMPLE 13

Two human patients with atopic dermatitis that responded poorly to topical and systemic corticosteroids and antihistamines were treated twice daily with Formula F for seven weeks. The treatment resulted in a complete clearing of the condition in both patients. The pruritis resolved in both patients within two weeks.

EXAMPLE 14

Seven patients suffering from inflammatory ichthyoses (lamellar, X-linked ichthyosis, or epidermolytic hyperkeratosis) were enrolled in a double blinded clinical study at San Francisco Veterans Hospital. The patients were treated for eight weeks with Formula E. Of the seven patients receiving Formula E, three experienced 100% clearance, and three more cleared by more than 50%. Among the placebo patients, only one cleared by more than 50%.

EXAMPLE 15

The subject of this example is a 14-year-old female yellow Labrador dog with a three-week history of a pruritic oozing erosion, 3.5 cm in diameter, surrounded by scaling, crusting and hair loss. The condition had progressed despite treatment with several veterinary products.

The animal was treated twice daily with Formula B. Within 24 hours, the animal had stopped licking and biting at the wound, and the inflammation was noticeably decreased. The lesion was completely healed in 7 days.

EXAMPLE 16

This example uses an animal model (hairless mice) to study DNA synthesis suppression.

Conventional methods for increasing DNA synthesis are topical exposure to ultraviolet C light or to phorbol ester. Both methods were used in this test. For stimulation by ultraviolet C, hairless mice about three months old were exposed to 12 watts/cm$^2$ of radiation for 9 minutes at a distance of 15 cm from the back skin surface. The test agents were then applied at 6 hours, 24 hours and 48 hours after the irradiation. One hour before sacrifice at 56 hours after the radiation, the mice were injected intraperitoneally with tritiated thymidine for scintillation counting to measure DNA synthesis suppression. For stimulation by phorbol ester, phorbol 12-myristate 13-acetate was applied to the backs of hairless mice which were also about 3 months old. Treatment agents were then applied 30 minutes, 6 hours, and 24 hours after the phorbol application. One hour prior to sacrifice at 56 hours, the mice were injected intraperitoneally with tritiated thymidine.

The test compounds were Kenalog 0.1% lotion (triamcinolone acetonide, E.R. Squibb & Sons, Princeton, N.J.), and monolaurin. Kenalog is a known antiinflammatory midpotency glucocorticosteroid and was used in these tests as a positive control. The monolaurin was tested in several formulations, including a 10% ethanol solution, a 7% ointment, a 5% ointment, a 3% ointment, a 1.5% ointment, and a 0.5% ointment.

The results are shown in Table I below. In the phorbol ester tests, the monolaurin 7% ointment and gel produced statistically significant reductions in tritiated thymidine uptake, indicating significant DNA synthesis suppression. The thymidine uptake inhibition produced by 10% monolaurin in ethanol was not significant. In Study A of the UVC tests, statistically significant inhibitions of thymidine uptake were produced by Kenalog 0.1% lotion (applied 1 or 3 times), monolaurin 7% ointment, 7% gel and 10% ethanol. In Study B of the UVC tests, all four concentrations of monolaurin ranging from 5% ointment to 0.5% ointment produced a statistically significant decrease of UVC stimulated thymidine uptake when compared to placebo. There were no statistically significant differences in inhibitory activity between the four concentrations tested, although the 0.5% ointment approached a statistically significant difference from 5% monolaurin with a probability of 0.06%.

The conclusion is that monolaurin produced a statistically significant inhibition of DNA synthesis as measured by thymidine uptake inhibition.

TABLE I

| DNA SYNTHESIS ASSAY RESULTS | | | | |
|---|---|---|---|---|
| Agent | Treated | Control | Inhibition | Probability |
| Average Radioactive Counts Per Animal - Phorbol Stimulated: | | | | |
| Monolaurin 7% Ointment | 5,138 | 8,922 | 42.41% | 0.20% |
| Monolaurin 7% Gel | 4,332 | 6,923 | 37.43% | 0.12% |
| Monolaurin 10% EtOH | 5,357 | 7,039 | 23.90% | 16.00% |
| Study A: | | | | |
| Average Radioactive Counts Per Animal - UVC Stimulated: | | | | |
| Kenalog 0.1% Lotion × 3 | 2,415 | 8,859 | 72.74% | <0.05% |
| Kenalog 0.1% Lotion × 1 | 3,155 | 8,276 | 61.88% | <0.05% |
| Kenalog 0.1% Lotion × 1 | 5,097 | 11,933 | 57.29% | 0.34% |
| Monolaurin 10% EtOH | 4,966 | 11,833 | 57.78% | <0.05% |
| Monolaurin 7% Gel | 5,010 | 8,035 | 37.65% | 0.33% |
| Monolaurin 7% Ointment | 4,655 | 8,035 | 41.94% | 0.46% |
| Study B: | | | | |
| Average Radioactive Counts Per Animal - UVC Stimulated: | | | | |
| Monolaurin 5% Ointment | 59,735 | 194,200 | 69.24% | <0.005% |
| Monolaurin 3% Ointment | 75,580 | 194,200 | 61.08% | <0.005% |
| Monolaurin 1.5% Ointment | 65,193 | 194,200 | 66.43% | <0.005% |
| Monolaurin 0.5% Ointment | 76,870 | 194,200 | 60.42% | <0.05% |

EXAMPLE 17

This example is a study of a test performed on mouse ears as a model for skin disease therapy.

Inflammation was induced in the ears of Swiss Webster mice 8-10 weeks old by applying phorbol 12-myristate 13-acetate. Test agents were then applied at fifteen minutes, 6 hours, and 24 hours after the phorbol application. Thirty hours after the phorbol application, the mice were sacrificed and 6 mm punches of the ears were taken.

Antiinflammatory activity was tested by measuring a decrease in weight and thickness of the mouse ears. The test compounds included in the test were:

Kenalog 0.1% lotion (triamcinolone acetonide, E. R. Squibb & Sons, Princeton, N.J.), a known antiinflammatory midpotency glucocorticosteroid Monolaurin The results are listed in Table II below.

TABLE II

ANTIINFLAMMATORY ASSAYS
Averages of Ten Different Mouse Ears

| Agent | Treated Ear | | Control Ear | | Treated Ear Decrease vs. Control | | | |
|---|---|---|---|---|---|---|---|---|
| | Thickness (mm) | Weight (g) | Thickness (mm) | Weight (g) | Decrease in Thickness (%) | Probability (%) | Decrease in Weight (%) | Probability (%) |
| Kenalog (0.1% Lotion) | 0.38 | 0.0127 | 0.56 | 0.0184 | 32.14 | <2 | 30.98 | <2 |
| Monolaurin | 0.42 | 0.0143 | 0.52 | 0.0153 | 19.23 | <2 | 6.54 | >5 |
| Control | 0.54 | 0.0199 | 0.54 | 0.0198 | 0.00 | >5 | −0.51 | >5 |

The foregoing description is offered primarily for purposes of illustration. It will be readily apparent to those skilled in the art that numerous variations in both the formulations and their methods of use beyond those mentioned above may be made without departing from the spirit and scope of the invention.

What is claimed is:

1. A method for the treatment of skin suffering from one or more disease conditions selected from the group consisting of noninfectious inflammatory skin diseases, thermal injuries, hyperpigmentation disorders and premalignant tumors caused by ultraviolet ration, x-ray radiation and viral infections, said method comprising applying to the affected area a topical formulation containing as the sole therapeutically effective agent a compound selected from the group consisting of esters and amides of monocarboxylic acids having 9 to 18 carbon atoms.

2. A method for the treatment of skin suffering from one or more disease conditions selected from the group consisting of ichthyoses, psoriasis, acne, rosacea, dermatitis, melasma, actinic lentigos and burns, said method comprising applying to the affected area a topical formulation containing as the sole therapeutically effective agent a compound selected from the group consisting of esters and amides of monocarboxylic acids having 9 to 18 carbon atoms.

3. A method for the treatment of skin suffering from one or more disease conditions selected from the group consisting of lamellar ichthyosis, epidermolytic hyperkeratosis, X-linked ichthyosis, and congenital ichthyosiform erythroderma, said method comprising applying to the affected area a topical formulation containing as the sole therapeutically effective agent a compound selected from the group consisting of esters and amides of monocarboxylic acids having 9 to 18 carbon atoms.

4. A method for the treatment of skin suffering from one or more disease conditions selected from the group consisting of actinic keratoses, Bowen's disease, lentigo maligna, Bowenoid papulosus, condylomatous dysplasia and condylomatous carcinoma insitu, said method comprising applying to the affected area a topical formulation containing as the sole therapeutically effective agent a compound selected from the group consisting of esters and amides of monocarboxylic acids having 9 to 18 carbon atoms.

5. A method in accordance with claims 1, 2, 3 or 4 in which the concentration of said compound in said formulation is from about 1% to about 35% by weight.

6. A method in accordance with claims 1, 2, 3 or 4 in which said compound is an ester or amide of a member selected from the group consisting of pelargonic acid, capric acid, undecanoic acid, lauric acid, tridecanoic acid, myristic acid, myristoleic acid, palmitic acid, palmitoleic acid, hexadecanoic acid, oleic acid, linoleic acid, linolenic acid, and octadecanoic acid.

7. A method in accordance with claims 1, 2, 3 or 4 in which said compound is selected from the group consisting of esters and amides of lauric acid.

8. A method in accordance with claims 1, 2, 3 or 4 in which said compound is an ester selected from the group consisting of glycerides, saccharides, and esters of methanol, ethanol, propylene glycol, and polyethylene glycol.

9. A method in accordance with claims 1, 2, 3 or 4 in which said compound is an ester selected from the group consisting of monoglycerides, triglycerides, hexaglycerides, decaglycerides and sucrose esters.

10. A method in accordance with claims 1, 2, 3 or 4 in which said compound is a member selected from the group consisting of monolaurin, monocaprin, monomyristin, monolinolein, diglycerol caprylate, triglycerol caprylate, triglycerol pelargonate, triglycerol caprate, triglycerol laurate, hexaglycerol caproate, hexaglycerol caprylate, hexaglycerol pelargonate, hexaglycerol caprate, hexaglycerol laurate, decaglycerol butyrate, decaglycerol caprylate, decaglycerol pelargonate, decaglycerol caprate, decaglycerol laurate, sucrose myristate, sucrose laurate, sucrose caprate, sucrose palmitate, sucrose elaidate, sucrose oleate and sucrose linoleate.

11. A method in accordance with claims 1, 2, 3 or 4 in which said compound is monolaurin.

12. A method in accordance with claims 1, 2, 3 or 4 in which said compound is an amide selected from the group consisting of capratoylamide, laurylamide, myristoleylamide, palmitoleylamide, capratoyl-N,N-dimethylamide, lauryl-N,N-dimethylamide, myristoleyl-N,N-dimethylamide, palmitoleyl-N,N-dimethylamide, linoleyl-N,N-dimethylamide, and octadecanoyl-N,N-dimethylamide.

13. A method in accordance with claims 1, 2, 3 or 4 in which said compound is lauryl-N,N-dimethylamide.

14. A method in accordance with claims 1, 2, 3 or 4 in which said formulation further includes a stratum corneum penetration enhancer.

15. A method for the treatment of a domesticated animal suffering from one or more disease conditions selected from the group consisting of inflammatory skin diseases, thermal injuries and premalignant tumors, said method comprising applying to an area of skin of said animal afflicted with such condition a topical formulation containing as the sole therapeutically effective agent a compound selected from the group consisting of esters and amides of monocarboxylic acids having 9 to 18 carbon atoms.

16. A method in accordance with claim 15 in which the concentration of said compound in said formulation is from about 1% to about 35% by weight.

* * * * *